(12) United States Patent
Foreman et al.

(10) Patent No.: US 10,413,508 B2
(45) Date of Patent: Sep. 17, 2019

(54) PREPARATION OF AN OIL-IN-WATER EMULSION FOR POLYMER STABILIZED PHARMACEUTICAL FORMULATIONS

(71) Applicant: R. P. Scherer Technologies, LLC, Las Vegas, NV (US)

(72) Inventors: James Michael Foreman, Crystal Lake, IL (US); Anayo Michael Ukeje, Skokie, IL (US); Ronald W. Swank, Crystal Lake, IL (US); Waiken Wong, Oak Park, IL (US)

(73) Assignee: R. P. Scherer Technologies, LLC, Las Vegas, NV (US)

( * ) Notice: Subject to any disclaimer, the term of this patent is extended or adjusted under 35 U.S.C. 154(b) by 0 days.

(21) Appl. No.: 15/546,205

(22) PCT Filed: Feb. 5, 2016

(86) PCT No.: PCT/US2016/016703
§ 371 (c)(1),
(2) Date: Jul. 25, 2017

(87) PCT Pub. No.: WO2016/127022
PCT Pub. Date: Aug. 11, 2016

(65) Prior Publication Data
US 2018/0049981 A1    Feb. 22, 2018

Related U.S. Application Data

(60) Provisional application No. 62/112,804, filed on Feb. 6, 2015.

(51) Int. Cl.
| | | |
|---|---|---|
| *A61K 9/127* | (2006.01) | |
| *A61K 9/107* | (2006.01) | |
| *A61K 38/13* | (2006.01) | |
| *A61K 47/10* | (2017.01) | |
| *A61K 47/44* | (2017.01) | |
| *A61K 31/436* | (2006.01) | |
| *A61K 31/337* | (2006.01) | |
| *A61K 31/05* | (2006.01) | |
| *A61K 31/165* | (2006.01) | |
| *A61K 31/343* | (2006.01) | |
| *A61K 31/365* | (2006.01) | |
| *A61K 31/395* | (2006.01) | |
| *A61K 31/4045* | (2006.01) | |
| *A61K 31/427* | (2006.01) | |
| *A61K 31/4745* | (2006.01) | |
| *A61K 31/475* | (2006.01) | |
| *A61K 31/675* | (2006.01) | |

(Continued)

(52) U.S. Cl.
CPC .......... *A61K 9/1075* (2013.01); *A61K 9/0048* (2013.01); *A61K 9/107* (2013.01); *A61K 31/05* (2013.01); *A61K 31/165* (2013.01); *A61K 31/337* (2013.01); *A61K 31/343* (2013.01); *A61K 31/365* (2013.01); *A61K 31/395* (2013.01); *A61K 31/4045* (2013.01); *A61K 31/427* (2013.01); *A61K 31/436* (2013.01); *A61K 31/475* (2013.01); *A61K 31/4745* (2013.01); *A61K 31/675* (2013.01); *A61K 31/7048* (2013.01); *A61K 31/7068* (2013.01); *A61K 38/13* (2013.01); *A61K 38/14* (2013.01); *A61K 47/10* (2013.01); *A61K 47/14* (2013.01); *A61K 47/26* (2013.01); *A61K 47/32* (2013.01); *A61K 47/36* (2013.01); *A61K 47/44* (2013.01); *A61K 51/122* (2013.01)

(58) Field of Classification Search
CPC ........ A61K 9/1075; A61K 9/10; A61K 9/107; A61K 9/113; A61K 9/1277
See application file for complete search history.

(56) References Cited

U.S. PATENT DOCUMENTS

| 5,474,979 A | 12/1995 | Ding et al. |
|---|---|---|
| 5,981,607 A | 11/1999 | Ding et al. |

(Continued)

FOREIGN PATENT DOCUMENTS

| CA | 2578176 A1 | 5/2006 |
|---|---|---|
| WO | WO2005027872 A2 | 3/2005 |

OTHER PUBLICATIONS

International Search Report and Written Opinion; dated Jun. 22, 2016 for PCT Application No. PCT/US2016/016703.

(Continued)

*Primary Examiner* — Micah Paul Young
(74) *Attorney, Agent, or Firm* — Mendelsohn Dunleavy, P.C.

(57) ABSTRACT

An improved process for producing an oil-in-water emulsion to deliver a substantially water insoluble active pharmaceutical ingredient includes creating a microemulsion containing such ingredient in the oil phase of the emulsion by mixing an aqueous phase including non-ionic surfactant, polyol, and water, wherein the weight ratio of the surfactant to polyol to water is between 10:20:70 and 1:1:1, to generate a mixture, with an oil phase comprising a substantially water insoluble active pharmaceutical ingredient and a long-chain triglyceride; circulating the said mixture through a homogenizer at a temperature from 20° C. to 60° C. to generate a coarse emulsion; passing the coarse emulsion through a microfluidizer at a pressure of from 70 MPa to 150 MPa at least once to produce an oil-in-water microemulsion; and, optionally, filtering the microemulsion through a 0.2 µm filter and/or mixing the microemulsion with a polymeric stabilizer.

19 Claims, 2 Drawing Sheets

(51) Int. Cl.
*A61K 31/7048* (2006.01)
*A61K 31/7068* (2006.01)
*A61K 9/00* (2006.01)
*A61K 47/26* (2006.01)
*A61K 47/32* (2006.01)
*A61K 47/36* (2006.01)
*A61K 38/14* (2006.01)
*A61K 47/14* (2017.01)
*A61K 51/12* (2006.01)

(56) References Cited

U.S. PATENT DOCUMENTS

| | | | |
|---|---|---|---|
| 6,114,319 A * | 9/2000 | Kimura | A61K 9/0048 514/177 |
| 6,379,688 B2 | 4/2002 | Yamaguchi et al. | |
| 8,557,861 B2 | 10/2013 | Chen | |
| 2001/0003003 A1 | 6/2001 | Yamaguchi et al. | |
| 2002/0107265 A1* | 8/2002 | Chen | A61K 9/1075 514/310 |
| 2006/0100288 A1* | 5/2006 | Bague | A61K 9/0048 514/642 |
| 2012/0135947 A1 | 5/2012 | Shikamura | |

OTHER PUBLICATIONS

Bhatt, P., and S. Madhav. "A detailed review on nanoemulsion drug delivery system." International Journal of Pharmaceutical sciences and research 2.9 (2011): 2292.

Shunmugaperumal, Tamilvanan, et al. "Manufacturing techniques and excipients used during the formulation of oil-in-water type nanosized emulsions for medical applications." Journal of Excipients and Food Chemicals 1.1 (2010): 11-29.

European Search Report; dated Jun. 29, 2018 for EP Application No. 16747314.9.

* cited by examiner

PREPARATION OF AN OIL-IN-WATER EMULSION FOR POLYMER STABILIZED PHARMACEUTICAL FORMULATIONS

FIELD OF THE INVENTION

The present invention is directed to a method of preparing an oil-in-water microemulsion which may be used for preparing medicaments or medicines that deliver a substantially water insoluble active pharmaceutical ingredient.

DESCRIPTION OF RELATED TECHNOLOGY

Emulsions, due to the physicochemical interactions of the oil droplets, have typically had stability problems. Some efforts have been made to overcome such problems.

An eye drop emulsion designed to alleviate dry eye related symptoms in dry eye patients and contact lens wearers is disclosed in U.S. Pat. No. 5,981,607. The composition includes an emulsion of a higher fatty acid glyceride, polysorbate 80 and an emulsion stabilizing amount of Pemulen® in water. The composition is suitable for topical application to ocular tissue.

Non-irritating emulsions for sensitive tissue are disclosed in U.S. Pat. No. 5,474,979. This pharmaceutical composition includes at least one cyclosporin in admixture with a higher fatty acid glyceride and polysorbate 80. The cyclosporin may be cyclosporin A and the higher fatty acid glyceride may be castor oil. Such a composition has been found to provide a high comfort level and low irritation potential that is suitable for delivery of medications to sensitive areas such as ocular tissue. In addition, the composition is stable for up to nine months without crystallization of cyclosporin.

A preservative for an emulsion and an emulsion containing the preservative is disclosed in U.S. Pat. No. 6,379,688. The preservative may include sorbic acid or a pharmaceutically acceptable salt thereof, sodium edetate and boric acid. The emulsion contains the preservative. The preservative is useful in oil-in-water (O/W) type emulsions. The addition of sodium edetate and boric acid is said to provide an emulsion having a high pH with superior preservation even at low concentration of the preservative. The oil-in-water emulsion may contain an emulsifier, an oil, a non-ionic surfactant, a buffering agent and an isotonizing agent. The median droplet size in the emulsion may be in the range of 1-0.001 µm. The active pharmaceutical ingredient is pirenoxine, which is used for treating or preventing cataracts. The process for making the emulsion includes (i) making an aqueous phase by dissolving Polysorbate 80, concentrated glycerin, sodium acetate, sorbic acid, boric acid and sodium edetate in water at 70° C.; (ii) making an oil phase by dissolving pirenoxine in castor oil at 70° C.; (iii) mixing the aqueous phase and oil phase in a homogenizer at 70° C. to give a crude emulsion; (iv) passing the crude emulsion through a microfluidizer to produce a fine emulsion with fine particles; and (v) filtering the fine emulsion to sterilize it.

Low oil emulsion compositions for delivering taxoids and other insoluble drugs are disclosed in U.S. Pat. No. 8,557,861. The injectable oil-in-water emulsion may comprise a taxoid drug or another water insoluble drug, an oil component at a concentration of at most about 6% by weight of the emulsion, and water. The oil component comprises a vegetable oil which may be a long chain triglyceride. The oil component may make up 1% to 6% by weight of the emulsion. The emulsion further comprises an emulsifier and glycerol. The emulsion has a small droplet size of from 50 to 250 nm, and may be sterilized by filtration through a 0.2 µm filter. The active pharmaceutical ingredient is paclitaxel, a cancer chemotherapy drug that is water insoluble. One process disclosed for making the emulsion comprises the steps of (i) making an oil phase by combining paclitaxel, soybean oil, medium chain triglyceride, and egg lecithin; (ii) making an aqueous phase by dissolving glycerin and glycine in water; (iii) mixing the aqueous phase and oil phase in a high shear mixer to give a crude emulsion, whose pH is adjusted to 6.5±0.2; (iv) passing the crude emulsion through a microfluidizer at an operating pressure of 18,000-23,000 psi; and (v) filtering the emulsion through a 0.2 µm filter.

Compositions containing difluprednate are taught in U.S. Pat. No. 6,114,319. A liquid composition comprising difluprednate, oil, water and an emulsifier is said to have superior anti-inflammatory and anti-allergic effects. Such a composition shows superior transfer to a lesion and uniform drug distribution upon administration, as compared to conventional preparations containing difluprednate, so that it shows sufficient efficacy in a smaller dose. The oil comprises a fatty acid ester of glycerol, such as castor oil, peanut oil, cotton seed oil, soybean oil, and olive oil. The emulsion further comprises a surfactant such as polysorbate. The droplets in the emulsion have a size of 1 to 0.001 µm with a pH of 3-8. The patent contemplates that the emulsion may further contain a water soluble polymer for enhancing stabilization of the emulsion. Water soluble polymers include povidone (polyvinylpyrrolidone), polyvinyl alcohol, hydroxyethylcellulose, hydroxypropylcellulose, methylcellulose, hydroxypropylmethylcellulose, carboxym ethylcellulose. An exemplary process for making an emulsion comprises the steps of: (i) making an aqueous phase by dissolving Polysorbate 80, polyvinyl alcohol, concentrated glycerol, sodium acetate, and benzalkonium chloride in water at 70° C.; (ii) adjusting the pH of the aqueous phase to 5.0 with hydrochloric acid; (iii) making an oil phase by dissolving difluprednate in castor oil at 70° C.; (iv) mixing the aqueous phase and oil phase in a homogenizer to give a crude emulsion; (v) passing the crude emulsion through a microfluidizer to produce a fine emulsion with fine particles; and (vi) filtering the fine emulsion to sterilization.

Ophthalmic emulsions containing an immunosuppressive agent are taught in Canadian Patent No. 2,578,176. These ophthalmic oil-in-water emulsions may comprise colloid particles having an oily core surrounded by an interfacial film. The emulsion may include an immunosuppressive agent, an oil, preferably at least 50% of which is MCT, and tyloxapol. These emulsions are useful for the manufacture of a medicament for treatment of eye conditions, particularly dry eye diseases. The oil may be a vegetable oil selected from olive, soy, corn, cottonseed, safflower, and sesame oil. The droplets in the emulsion have a particle size of less than 300 nm, or in the range of 100 to 250 nm.

SUMMARY OF THE INVENTION

The present invention relates to a novel process for the preparation of a stable emulsion. This process is particularly suitable for the preparation of polymer-stabilized pharmaceutical formulations. More specifically, the present invention provides a process for producing an oil-in-water (O/W) microemulsion that has improved long-term stability without the need of using polymeric stabilizers, harsh solvents or high levels of surfactant.

The process of the invention utilizes a recirculation loop with integrated high and low pressure homogenization and temperature/pressure control. One aspect of the present invention is a method of preparing an oil-in-water microemulsion including steps of: (a) mixing an aqueous phase comprising non-ionic surfactant, polyol, and water, wherein the weight ratio of the surfactant to polyol to water is between 1:2:7 and 1:1:1, with an oil phase comprising a substantially water insoluble active pharmaceutical ingredient in a long-chain triglyceride to form a first mixture; (b) passing the first mixture through a homogenizer at a temperature of from about 20° C. to about 60° C. to generate a coarse emulsion; and (c) passing the coarse emulsion at least once through a microfluidizer at a pressure of from about 70 MPa to about 150 MPa to produce an oil-in-water microemulsion, wherein the mean oil particle droplet size is between about 1 nm and 300 nm and the weight ratio of the oil phase to the aqueous phase is between about 0.01:1 and 1:1.

In a second aspect of the present invention, the non-ionic surfactant is a polyoxyethylene derivative of a sorbitan ester.

In a third aspect, the non-ionic surfactant is polysorbate 80.

In a fourth aspect, the polyol is a sugar alcohol.

In a fifth aspect, the polyol is a glycerol.

In a sixth aspect, the weight ratio of the surfactant to polyol to water is between 1:2:7 and 17:24:59.

In a seventh aspect, the weight ratio of the surfactant to polyol to water is between 17:28:55 and 25:33:42.

In an eighth aspect, the weight ratio of the surfactant to polyol to water is between 25:24:51 and 33:28:39.

In a ninth aspect, the weight ratio of the oil phase to the aqueous phase is between about 0.01:1 and 0.1:1.

In a tenth aspect, the active pharmaceutical ingredient is selected from the group consisting of: paclitaxel, docetaxel, ortataxel taxane, epothilone, camptothecin, colchicine, geladanamycin, amiodarone, thyroid hormone, amphotericin, corticosteroid, propofol, melatonin, cyclosporine, rapamycin, tacrolimus, mycophenolic acid, ifosfamide, vinorelbine, vancomycin, gemcitabine, thiotepa, bleomycin, a substantially water insoluble diagnostic radiocontrast agents, and mixtures thereof.

In an eleventh aspect, the active pharmaceutical ingredient is cyclosporine.

In a twelfth aspect, a further step in the method of making the emulsion comprises filtering the microemulsion through a 0.2 μm filter.

In a thirteenth aspect, a further step in the method of making the emulsion comprises mixing the microemulsion with a polymeric stabilizer.

In a fourteenth aspect, the polymeric stabilizer is selected from the group consisting of: polyvinyl alcohol, polyvinyl acetal, polyvinylpyrrolidone, and polysaccharide.

DETAILED DESCRIPTION OF THE INVENTION

Figure 1:
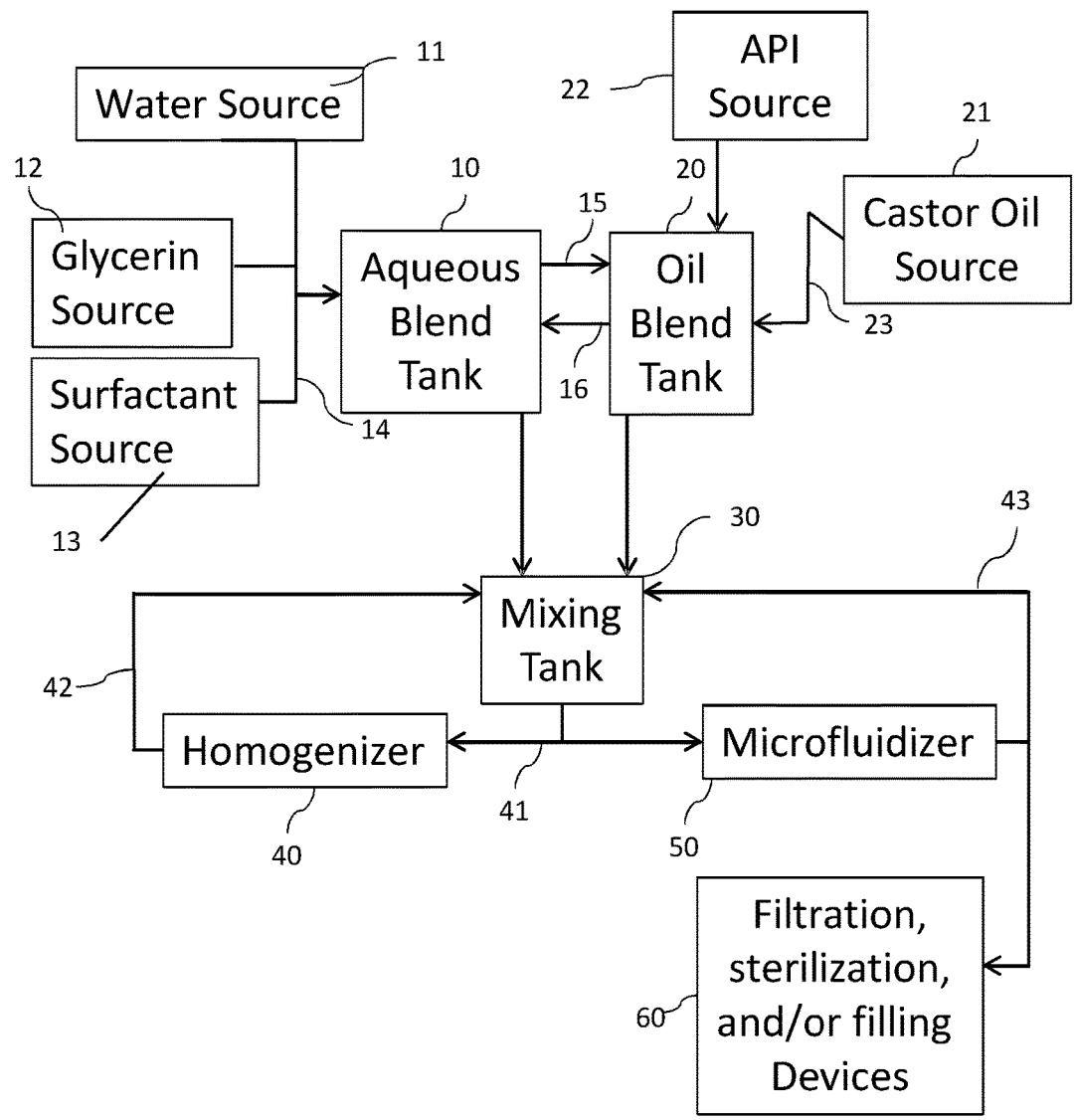
FIG. 1 shows a schematic representation of an exemplary apparatus used to prepare the oil-in-water microemulsion of the present invention.

The present invention relates to a process for preparation of a stable emulsion, preferably an oil-in-water emulsion. Such a process is particularly suitable for preparation of polymer stabilized pharmaceutical formulations.

More specifically, the present invention provides a process for producing an oil-in-water microemulsion that has improved long-term stability as compared to compositions that employ, for example, polymeric stabilizers, harsh solvents or high levels of surfactant. The microemulsion comprises a discontinuous oil phase containing an active pharmaceutical ingredient dissolved in a long-chain triglyceride, and a continuous aqueous phase comprising an excipient and a surfactant dissolved in water. The mean droplet size of the discontinuous oil phase is preferably between 50 and 120 nm.

The invention also provides a fully formulated pharmaceutical microemulsion. One of the advantages of the microemulsion is that it has a relatively small droplet size. The smaller droplet size provides an improvement in the bioavailability of the active pharmaceutical ingredient dissolved in the oil by increasing the surface area of the droplets that can participate in delivery of the active pharmaceutical ingredient. This may be important in ophthalmic preparations or topical preparations.

The term "water" as used herein means pure water, distilled water, or water that may be used in preparation of pharmaceutical substances, or water as specified as such by a recognized compendium. The term "water" as used in terms such as "oil-in-water" means aqueous, i.e. is not limited to pure water but may also encompass a phase that is largely water but may contain other ingredients as well, preferably with such other ingredients being present in solution in the aqueous phase.

"Microemulsion" as used in this specification and the appended claims includes the common definition of a microemulsion, namely, a dispersion made of water, oil and surfactant that is anisotropic and thermodynamically stable with dispersed droplet diameters in the range of 1 to 300 nm, preferably 10 to 100 nm.

The phrase "droplet size" means the median diameter (D50) for the volume distribution of the discontinuous oil droplets in the aqueous phase. Determination of D50 may be performed by a light diffraction method such as ISO 13320: 2009, and can be calculated by means presented in ISO 9276-2:2014. The D50 may also be determined using ASTM E799-3(2009).

The phrase "active pharmaceutical ingredient" includes any substance or mixture of substances intended to be used in the manufacture of a drug (medicinal) product or a substance that when used in the production of a drug becomes an active ingredient of the drug product. Such substances are intended to furnish pharmacological activity or other direct effect in the diagnosis, cure, mitigation, treatment or prevention of disease or to affect the structure or function of the human or animal body.

The term "microfluidized", "microfluidizing", or "microfluidizer" as used herein refers to an instrument or a process that utilizes a continuous turbulent flow at high pressure to fluidize a material, including a microfluidizer or other like device that may be useful in creating a microemulsion having the droplet sizes specified herein. A typical microfluidizer may comprise a fluid inlet, an air motor pumping at a high pressure, and an interaction chamber where multiple channels of fluid flow at high velocity and collide with each other. Typically, a microfluidizer may be operated at a pressure of approximately 25,000 psi to generate a microemulsion.

It must be noted that as used in the present specification and the appended claims, the singular forms "a", "an", and "the" include plural references unless the context clearly dictates otherwise. Furthermore, the terms "a" (or "an"), "one or more," and "at least one" can be used interchangeably herein. The term "comprising" indicates open to inclusion of other materials or components without limitation. The terms "comprising," "including," "having," and "constructed from" can also be used interchangeably.

Unless otherwise indicated, all numbers expressing quantities of ingredients, properties such as molecular weight, percent, ratio, reaction conditions, and so forth used in the specification and claims are to be understood as being modified in all instances by the term "about," whether or not the term "about" is present. Accordingly, unless indicated to the contrary, the numerical parameters set forth in the specification and claims are approximations that may vary depending upon the desired properties sought to be obtained by the present disclosure. At the very least, and not as an attempt to limit the application of the doctrine of equivalents to the scope of the claims, each numerical parameter should at least be construed in light of the number of reported significant digits and by applying ordinary rounding techniques. Notwithstanding that the numerical ranges and parameters setting forth the broad scope of the disclosure are approximations, the numerical values set forth in the specific examples are reported as precisely as permitted by the measuring equipment that was used. Any numerical value in the specific examples, however, inherently contains certain errors necessarily resulting from the standard deviation found in their respective testing measurements.

It is to be understood that each component, compound, substituent or parameter disclosed herein is to be interpreted as being disclosed for use alone or in combination with one or more of each and every other component, compound, substituent or parameter disclosed herein.

It is also to be understood that each amount/value or range of amounts/values for each component, compound, substituent or parameter disclosed herein is to be interpreted as also being disclosed in combination with each amount/value or range of amounts/values disclosed for any other component(s), compounds(s), substituent(s) or parameter(s) disclosed herein and that any combination of amounts/values or ranges of amounts/values for two or more component(s), compounds(s), substituent(s) or parameters disclosed herein are thus also disclosed in combination with each other for the purposes of this description.

It is further understood that each range disclosed herein is to be interpreted as a disclosure of each specific value within the disclosed range that has the same number of significant digits. Thus, a range of from 1-4 is to be interpreted as an express disclosure of the values 1, 2, 3 and 4.

It is further understood that each lower limit of each range disclosed herein is to be interpreted as disclosed in combination with each upper limit of each range and each specific value within each range disclosed herein for the same component, compounds, substituent or parameter. Thus, this disclosure to be interpreted as a disclosure of all ranges derived by combining each lower limit of each range with each upper limit of each range or with each specific value within each range, or by combining each upper limit of each range with each specific value within each range.

Furthermore, specific amounts/values of a component, compound, substituent or parameter disclosed in the description or an example is to be interpreted as a disclosure of either a lower or an upper limit of a range and thus can be combined with any other lower or upper limit of a range or specific amount/value for the same component, compound, substituent or parameter disclosed elsewhere in the application to form a range for that component, compound, substituent or parameter.

An aspect of the present invention is a process that provides a stable microemulsion. Such a stable microemulsion minimizes or prevents creaming and coalescence of the oil droplets. Further, the emulsion of the present invention may provide better bioavailability without requiring additional stabilization of the emulsion.

One aspect of the present invention is a method of preparing an oil-in-water microemulsion, comprising the steps of: (a) mixing an aqueous mixture comprising a polyol, a non-ionic surfactant and water, with an oil mixture comprising a water-insoluble active pharmaceutical ingredient and a long chain triglyceride, to generate a mixture; (b) passing the mixture generated in step (a) through a homogenizer at a temperature of from about 20° C. to about 60° C. to generate a coarse emulsion; and (c) passing the coarse emulsion at least once through a microfluidizer.

The process permits a user to manipulate the oil droplet size by adjusting the number of times the composition is recirculated through a homogenizer such as a low pressure in-line or top-entering homogenizer, the temperature, and the parameters of the microfluidization process. The emulsion process of the present invention allows for more precise process control In certain embodiments, the microfluidizer is operated at a pressure of from 70 MPa to 150 MPa to produce the oil-in-water microemulsion.

In some embodiments, the mean oil particle size is between about 1 nm and about 300 nm; wherein the weight ratio of a polyol to water is between about 1:1 to about 0.25:1, the weight ratio of the surfactant to water is between about 1:1 to about 0.15:1, and the weight ratio of the aqueous phase to the oil phase is between about 1:1 and about 99:1.

In some embodiments, the oil phase to aqueous phase is a ratio of 3 to 7 wt % of oil phase to 97 to 93 wt % of aqueous phase, and the aqueous phase comprises 3 to 5 wt % surfactant.

The method of preparing an oil-in-water microemulsion comprises at least three sequential steps: a mixing step, a homogenizing step and a microfluidizing step.

The Mixing Step

In the mixing step, an aqueous phase comprising a polyol, at least one non-ionic surfactant, and water, is mixed in a mixing tank with an oil phase comprising a long-chain triglyceride and a substantially water-insoluble active ingredient. Upon mixing the aqueous phase with the oil phase, a mixture is produced.

The Aqueous Phase

In one embodiment of the present invention, water from a water supply (11), the polyol from a polyol supply tank (12) and one or more non-ionic surfactants from the surfactant supply tank (13) are introduced at certain ratios via an aqueous tank manifold (14) into an aqueous blend tank (10). Alternatively, one or more of these three ingredients may be introduced into the aqueous blend tank (10) by a different means. For example, each of the water, polyol and non-ionic surfactant may be added to the aqueous blend tank (10) via individual inlets.

In order to obtain a stable microemulsion in accordance with the present invention, the weight ratios of the ingredients need to be selected appropriately. The ratio of the non-ionic surfactant to the polyol appears to be important to formation of the microemulsion of the present invention. Such a selection depends, to some extent, on the identity of the active pharmaceutical ingredient, and the identity of the non-ionic surfactant.

Unlike many other oil-in-water emulsions, the aqueous phase of the present emulsion comprises relatively high levels of non-ionic surfactant and polyol, and relatively lower amounts of water. The weight ratio of the non-ionic surfactant to the polyol to the water in the aqueous phase used to make the microemulsion of the present invention is in the range of 10:20:70 to 1:1:1.

One example of an aqueous phase of the present invention comprises 10 to 17 wt % non-ionic surfactant and 20 to 24 wt % polyol, with the balance being water. A second example of an aqueous phase of the present invention comprises 10 to 17 wt % non-ionic surfactant and 24 to 28 wt % polyol, with the balance being water. A third example of an aqueous phase of the present invention comprises 10 to 17 wt % non-ionic surfactant and 28 to 35 wt % polyol, with the balance being water. A fourth example of an aqueous phase of the present invention comprises 17 to 25 wt % non-ionic surfactant and 20 to 24 wt % polyol, with the balance being water. A fifth example of an aqueous phase of the present invention comprises 17 to 25 wt % non-ionic surfactant and 24 to 28 wt % polyol, with the balance being water. A sixth example of an aqueous phase of the present invention comprises 17 to 25 wt % non-ionic surfactant and 28 to 35 wt % polyol, with the balance being water. A seventh example of an aqueous phase of the present invention comprises 25 to 35 wt % non-ionic surfactant and 20 to 24 wt % polyol, with the balance being water. An eighth example of an aqueous phase of the present invention comprises 25 to 35 wt % non-ionic surfactant and 24 to 28 wt % polyol, with the balance being water. A ninth example of an aqueous phase of the present invention comprises 25 to 35 wt % non-ionic surfactant and 28 to 35 wt % polyol, with the balance being water.

The polyol of the present invention is a pharmaceutically acceptable compound containing multiple hydroxyl groups. Examples of polyols include sugar alcohols. Examples of sugar alcohols are triols, such as glycerol; tetraols, such as erythritol, threitol; pentaols, such as arabitol, xylitol, ribitol; hexaols, such as mannitol, sorbitol, galactitol, fucitol, iditol, inositol; heptaols, such as volemitol, dodecaols, such as isomalt, maltitol, lactitol; octadecanols, such as maltotriitol; and tetracosanols, such as maltotetraitol. Glycerol is also known as glycerin, glycerine, propanetriol, and 1,2,3-trihydroxypropane. In one embodiment of the invention, the polyol is a sugar alcohol. In another embodiment of the invention, the polyol is a glycerol.

The identity of the non-ionic surfactant and the loading levels thereof play a role in determining the droplet size of the microemulsion. Examples of suitable non-ionic surfactants include the condensation products of alkylene oxides with fatty acids (i.e., alkylene oxide esters of fatty acids), the condensation products of one mole of alkylene oxide with two moles of fatty acids (i.e., alkylene oxide diesters of fatty acids), the condensation products of alkylene oxides with fatty alcohols (i.e., alkylene oxide ethers of fatty alcohols), and the condensation products of alkylene oxides with both fatty acids and fatty alcohols. Nonlimiting examples of these alkylene oxide derived nonionic surfactants include ceteth-6, ceteth-10, ceteth-12, ceteareth-6, ceteareth-10, ceteareth-12, steareth-6, steareth-10, steareth-12, steareth-21, PEG-6 stearate, PEG-10 stearate, PEG-100 stearate, PEG-12 stearate, PEG-20 glyceryl stearate, PEG-80 glyceryl tallowate, PEG-10 glyceryl stearate, PEG-30 glyceryl cocoate, PEG-80 glyceryl cocoate, PEG-200 glyceryl tallowate, PEG-8 dilaurate, PEG-10 distearate, and mixtures thereof.

Additional examples of suitable nonionic surfactants include polyhydroxy fatty acid amide surfactants, sugar esters and polyesters, alkoxylated sugar esters and polyesters, $C_1$-$C_{30}$ fatty acid esters of $C_1$-$C_{30}$ fatty alcohols, alkoxylated derivatives of $C_1$-$C_{30}$ fatty acid esters of $C_1$-$C_{30}$ fatty alcohols, alkoxylated ethers of $C_1$-$C_{30}$ fatty alcohols, polyglyceryl esters of $C_1$-$C_{30}$ fatty acids, $C_1$-$C_{30}$ esters of polyols, $C_1$-$C_{30}$ ethers of polyols, alkyl phosphates, polyoxyalkylene fatty ether phosphates, fatty acid amides, acyl lactylates, polyethylene glycol 20 sorbitan monolaurate (Polysorbate 20), polyethylene glycol 5 soya sterol, Steareth-20, Ceteareth-20, PPG-2 methyl glucose ether distearate, Ceteth-10, Polysorbate 80, cetyl phosphate, diethanolamine cetyl phosphate, Polysorbate 60, glyceryl stearate, polyoxyethylene 20 sorbitan trioleate (Polysorbate 85), sorbitan monolaurate, polyglyceryl-4 isostearate, hexyl laurate, PPG-2 methyl glucose ether distearate, fatty acid ester blends based on a mixture of sorbitan or sorbitol fatty acid ester and sucrose fatty acid ester.

In one embodiment, the non-ionic surfactant is a polyoxyethylene derivative of a sorbitan ester, such as polysorbate 80 (Tween™ 80) and polysorbate 20 (Tween™ 20). In another embodiment, the non-ionic surfactant is polysorbate 80.

Additional water-soluble ingredients may be added to the aqueous blend tank (10), as may be needed to solubilize the contents of the aqueous blend tank (10), or to aid in formation of the final product. Such water-soluble ingredients may be added to the aqueous blend tank (10) via an inlet, or via the aqueous tank manifold.

The water, polyol, one or more surfactants, and any optional water-soluble ingredient(s) are blended in the aqueous blend tank to obtain an aqueous phase. The desired goal of blending is to fully solubilize the components in the aqueous phase. The blending may be as vigorous or as long as required to achieve full solubilization of the components in the aqueous phase as typically determined by visual inspection. The blending may be carried out at any temperature suitable to obtain a homogeneous or substantially homogeneous blend. Typical blending temperatures range from 20° C. to 60° C. Because water, polyol and surfactants are typically fully miscible, homogeneity is readily achieved.

Oil Phase

Long-chain triglyceride from a long-chain triglyceride supply tank (21) and the active pharmaceutical ingredient from an active pharmaceutical ingredient source (22) are added to the oil blend tank (20). Additional oil-soluble ingredients may be added to the oil blend tank (20), as may be needed to solubilize the contents of the oil blend tank (20), or to aid in formation of the final product.

The long-chain triglyceride and the active pharmaceutical ingredient may be added to the oil blend tank (20) via an oil tank manifold (23), as illustrated in FIG. 1. In cases where the active pharmaceutical ingredient is a solid, such as a crystalline solid or a powder, the active pharmaceutical ingredient is added to the oil tank via an inlet port.

The long-chain triglyceride and the active pharmaceutical ingredient, plus any optional oil-soluble ingredients are blended in the oil blend tank (20) to obtain an oil phase. The oil phase is a homogeneous blend of the ingredients in the oil blend tank (20). The blending may be done at any temperature, pressure, speed, or duration suitable to obtain a homogeneous blend. Typical blending temperatures may range from 50° C. to 70° C. In cases where the active pharmaceutical ingredient and the long-chain triglyceride are not readily miscible, achieving homogeneity may be more difficult, thus higher temperatures, higher pressures, higher blending speeds, or a longer blending time may be required.

The oil phase comprises a substantially water insoluble active pharmaceutical ingredient. The phrase "substantially water insoluble" when referring to the active pharmaceutical ingredient, means that the active pharmaceutical ingredient does not dissolve in water in detectable amounts, or the active pharmaceutical ingredient dissolves in water in amounts that are smaller than would be practical to administer to, for example, a human or animal needing or desiring said active pharmaceutical ingredient.

Further, because the volume of a dosage comprising an effective amount of the active pharmaceutical ingredient is dictated by the administration route, the phrase "substantially water insoluble" will also vary with the administration route. For example, an ophthalmic dosage of one drop (about 50 µL) needs to have about 300 times greater concentration to administer to a patient the same amount of active pharmaceutical ingredient as an oral dosage of one tablespoon (about 15 m); thus, if an efficacious amount of the active pharmaceutical ingredient dissolves in 1 mL, such active pharmaceutical ingredient would be considered as "substantially water insoluble" for ophthalmic dosage of one drop, but not for an oral dosage of one tablespoon.

The solubility in water of the substantially water insoluble active pharmaceutical ingredient at 20° C. may be less than about 10 g/L, including, for example, less than about any of 5, 2, 1, 0.5, 0.2, 0.1, 0.05, 0.02, or 0.01 g/L. In some embodiments, the substantially water insoluble pharmaceutical ingredient is a solid. In some embodiments, the substantially water insoluble pharmaceutical ingredient is a liquid.

Suitable active pharmaceutical ingredients include anticancer or antineoplastic agents, antimicrotubule agents, immunosuppressive agents, anesthetics, hormones, agents for use in cardiovascular disorders, antiarrhythmics, antibiotics, antifungals, antihypertensives, antiasthmatics, anti-inflammatory agents, anti-arthritic agents, vasoactive agents, analgesics/antipyretics, antidepressants, antidiabetics, antifungal agents, anti-inflammatories, antianxiety agents, immunosuppressive agents, antimigraine agents, sedatives, antianginal agents, antipsychotic agents, antimanic agents, antiarthritic agents, antigout agents, anticoagulants, thrombolytic agents, antifibrinolytic agents, hemorheologic agents, antiplatelet agents, anticonvulsants, antiparkinson agents, antihistamines/antipruritics, agents useful for calcium regulation, antiviral agents, antimicrobials, anti-infectives, bronchodilatators, hormones, hypoglycemic agents, hypolipidemic agents, antiulcer/antireflux agents, antinauseants/antiemetics, and oil-soluble vitamins (e.g., vitamins A, D, E, K, and the like).

Examples of substantially water insoluble active pharmaceutical ingredients that are well suited to the methods of the present invention include taxanes (such as paclitaxel, docetaxel, ortataxel and other taxanes), epothilones, camptothecins, colchicines, geladanamycins, amiodarones, thyroid hormones, amphotericin, corticosteroids, propofol, melatonin, cyclosporine, rapamycin (sirolimus), tacrolimus, mycophenolic acids, ifosfamide, vinorelbine, vancomycin, gemcitabine, thiotepa, bleomycin, and diagnostic radiocontrast agents, and mixtures, analogs or derivatives of any of the foregoing.

In some embodiments, the substantially water insoluble active pharmaceutical ingredient is preferably selected from paclitaxel, docetaxel, CY196, ortataxel or other taxane or taxane analog, 17-allyl amino geldanamycin (17-AAG), 18-derivatized geldanamycin, camptothecin, propofol, amiodarone, cyclosporine, epothilone, radicicol, combretastatin, rapamycin, amphotericin, liothyronine, epothilone, colchicine, thiocolchicine and its dimers, thyroid hormone, vasoactive intestinal peptide, corticosteroids, melatonin, tacrolimus, mycophenolic acids, epothilones, radicicols, and combretastatins, and mixtures, analogs or derivatives of any of the foregoing.

The long-chain triglyceride acts in the present invention as a solvent to solubilize or suspend the active pharmaceutical ingredient. In this specification, a long-chain triglyceride is a triglyceride whose fatty acid component is made up of long-chain fatty acids. Suitable long-chain fatty acids will contain more than 12 carbon atoms, preferably from 14 to 20 carbon atoms, or even more preferably from 14 to 18 carbon atoms. Examples of suitable long-chain triglycerides include pharmaceutically acceptable vegetable oils, for example canola, coconut, corn, cottonseed, flaxseed, olive, palm, peanut, safflower, sesame, soy and sunflower oils, glyceryl tri-stearate, glyceryl tri-palmitate, sunflower oil, castor oil, rape-seed oil, and mixtures of such oils. Oils of animal, particularly marine animal, origin can also be used, including for example fish oil.

Mixing Tank

A selected amount of the aqueous phase from the aqueous blend tank (10) is introduced into the mixing tank (30), and a selected amount of the oil phase from oil phase tank is introduced into the mixing tank. The addition may be done sequentially, or simultaneously.

In addition to the aforementioned surfactant to polyol to water ratio, selection of the ratio of the oil phase to the aqueous phase is also important to obtain a viable microemulsion. The weight ratio of the oil phase to the aqueous phase is in the range of 0.01:1 to 1:1. In one embodiment, the weight ratio of the aqueous phase to the oil phase is in the range of 0.01:1 and 0.10:1. Under another embodiment the weight ratio of the surfactant to water is in the range of 0.10:1 to 0.50:1. Under yet another embodiment the weight ratio of the surfactant to water is in the range of 0.50:1 and 1.00:1.

In cases where the entire contents of one of the blend tanks (10, 20) is emptied into the mixing tank, a selected amount of the other phase may be used to rinse the empty tank. For example, in cases where the active pharmaceutical ingredient is expensive, after emptying the oil blend tank (200, an amount of the aqueous phase can be introduced via a line (15) to rinse out at least part of the residue of the oil phase in the oil blend tank (20). Alternatively, a portion of the oil phase may be introduced into the aqueous blend tank (10) via a line (16) to rinse out at least part of the residue of the aqueous phase in the aqueous blend tank (10).

The aqueous phase and the oil phase are mixed in the mixing tank to generate a first mixture. This first mixture is an oil-in-water emulsion, wherein the water is the continuous phase and the oil is the discontinuous phase. The emulsion may be unstable on the time scale of minutes to hours, exhibiting complete phase separation. The mean droplet size of the coarse emulsion may be any size from 1 micrometer and larger.

Homogenization Step

After the aqueous phase and the oil phase are mixed to generate the first mixture, the first mixture is fed into a homogenizer (40). The homogenizer (40) adds energy to the first mixture to turn the first mixture into an emulsion with typical droplet sizes greater than 500 nm but less than $10^2$ micrometers. The emulsion is stable and unlikely to phase separate.

As exemplified in FIG. 1, the first mixture is continuously fed from the mixing tank discharge manifold (41) into the homogenizer (40). The first mixture is further emulsified by the homogenizer (40), and is continuously circulated back into the mixing tank (30) by return piping (42).

Selection of the pressure and temperature at which the homogenizer operates largely depends on the identities of the active pharmaceutical ingredient and surfactant, and one or more of the blending ratios. A typical pressure of a homogenizer (40) is between about 25 MPa and about 50 MPa (about 3600 psi to about 7200 psi). In one embodiment, the temperature of the product being fed into the homogenizer (40) is maintained between 20° C. and 60° C. in the mixing tank. In another embodiment, the temperature of the product being fed into the homogenizer (40) is between 30° C. and 50° C. In another embodiment, the temperature of the product being fed into the homogenizer is between 40° C. and 50° C.

The resulting coarse emulsion has a droplet size that is significantly smaller than the droplet size of the first mixture. The mean droplet size of the coarse emulsion is typically in the range of about 0.5 µm to about 5 µm.

The product is continuously circulated from the mixing tank (30) into the homogenizer (40) and back into the mixing tank by return piping (42). The circulation of the mixture into the homogenizer gradually decreases the droplet size of the composition residing in the mixing tank (30), so that the composition has a particle size that asymptotically approaches the particle size of the coarse emulsion. When a sufficient amount of recirculation time has passed, the mixing tank (30) will contain the composition that is indistinguishable from the coarse emulsion generated by the homogenizer (40), and is thus itself considered to be a coarse emulsion.

The term "homogenizer" means a piece of equipment that is used to homogenize the first mixture by exposing the first mixture to high shear conditions. In one embodiment of the present application, the homogenizer is a piece of equipment used in a production facility that homogenizes the first mixture by high shear.

Any kind of an in-line pilot plant homogenizer, or production homogenizer, or industrial homogenizer may be used. Examples of suitable homogenizers include Gaulin (manufactured by A.P.V Gaulin Inc.), Nanomizer (manufactured by Nanomizer Inc.), Sonolator (Sonic Corp.), Altimizer (produced by Sugino Machine) and DeBee (manufactured by Bee International Ltd.).

Microfluidizing Step

After the formation of the coarse emulsion by the use of a homogenizer, the coarse emulsion is passed through a microfluidizer at a pressure of from about 125 MPa to about 150 MPa at least once to produce an oil-in-water microemulsion. The emulsion process of the present invention may optionally utilize a recirculation loop with integrated temperature/pressure control to allow adjustment based on process requirements.

As exemplified in FIG. 1, the coarse emulsion in the mixing tank (30) is directed through the mixing tank discharge manifold (41) into the microfluidizer (50), where the coarse emulsion is transformed by the microfluidizer into a microemulsion. The microemulsion is then either circulated back into the mixing tank (30) by return piping (43), or is processed further by, for example, filtering, sterilizing and/or filling (60). The microemulsion can be sterilized by filtration through a 0.2 µm filter (hydrophilic PES or PVDF). The microemulsion can be combined with a sterile bulk polymeric solution containing cross-linked polyacrylic acid to provide further stabilization of the emulsion.

Selection of the pressures and temperatures at which the microfluidizer operates largely depends on the identities of the active pharmaceutical ingredient and/or the surfactant, and one or more of the aforementioned blending ratios, and the droplet size of the coarse emulsion. A typical working pressure of the microfluidizer is between about 125 MPa (about 18,000 psi) and about 150 MPa (about 21,600 psi).

The coarse emulsion is passed through the microfluidizer with the emulsion at a temperature of from about 20° C. to about 60° C. to generate a microemulsion. In one embodiment, the operating temperature of the homogenizer is between 20° C. and 40° C. In another embodiment, the operating temperature of the homogenizer is between 30° C. and 50° C. In another embodiment, the operating temperature of the homogenizer is between 40° C. and 60° C.

The resulting microemulsion has a droplet size that is significantly smaller than the droplet size of the coarse emulsion. Typically, the microemulsion appears translucent or clear. The mean droplet size of the microemulsion is in the range of from about 50 nm to about 120 nm. In one embodiment, the mean droplet size of the microemulsion is in the range of 50 nm and 70 nm. In another embodiment, the mean droplet size of the microemulsion is in the range of 70 nm and 90 nm. In another embodiment, the mean droplet size of the microemulsion is in the range of 90 nm and 120 nm.

Any kind of an in-line pilot plant microfluidizer, or production microfluidizer, or industrial microfluidizer may be used. An example of a microfluidizer is the Microfluidizer from Microfluidics Corp.

In one embodiment of the present invention, the microemulsion produced by the microfluidizer (50) is subjected to additional processing. Such additional processing may include one or more of the optional steps of filtration, sterilization, and filling of the microemulsion into commercial units. The final pharmaceutical product will be formulated to meet the quality target profile necessary for the indication that it will be used to treat. The aqueous and oil phases described herein are components of the final pharmaceutical product and are concentrates that are typically diluted to provide the final pharmaceutical product. For most pharmaceutical product properties, e.g. viscosity, assay, pH and osmolality, the formulation will require this final dilution step to meet the specifications for the formulation. Thus, the physicochemical properties of the concentrates are different from those of the final pharmaceutical formulations. Also, due to the dilution, the concentrations of the various components in the concentrates will be lowered in the final pharmaceutical formulation.

The dilution can be done with a variety of aqueous media, depending on the particular manufacturing process employed to make the concentrates and/or final pharmaceutical formulations. The dilution medium could be just an aqueous media or it could be the polymeric stabilizer-containing phase described above.

In another embodiment of the present invention, the microemulsion produced by the microfluidizer (50) is returned into the mixing tank (30) by the return piping (43), and after circulating two or more times through the microfluidizer, the droplet size of the composition residing in the mixing tank (30) gradually decreases. Once the desired droplet size is achieved, the microemulsion can then be sent for further processing. An advantage of using continuous recirculation to obtain the microemulsion, as compared to passing the coarse emulsion through the microfluidizer only once, is that recirculating the microemulsion through the microfluidizer will achieve smaller droplet sizes than could be achieved by a single pass.

Figure 2:
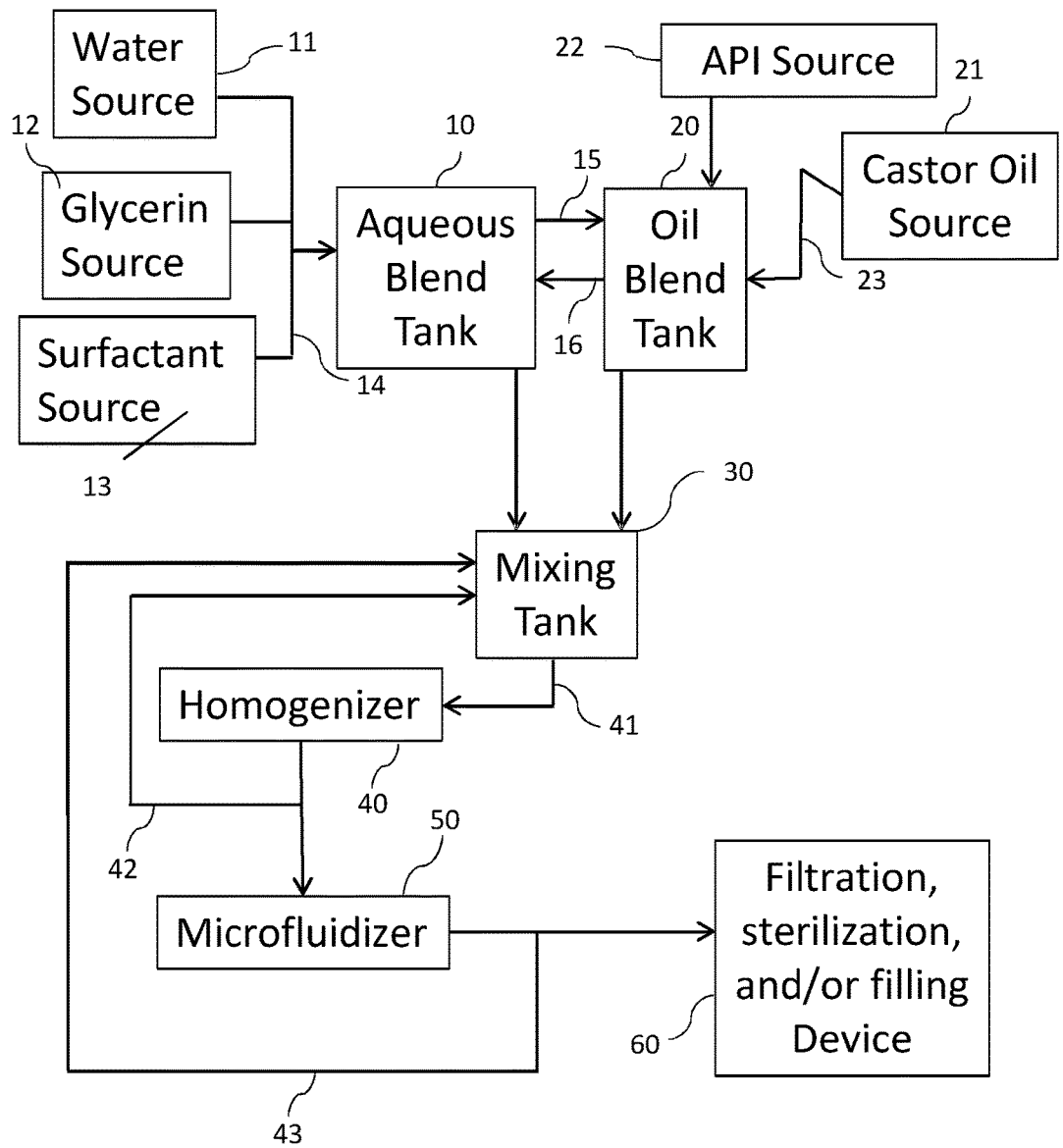
FIG. 2 shows a schematic representation of an alternative exemplary apparatus used to prepare the oil-in-water microemulsion of the present invention.

An alternative embodiment of the present invention is illustrated in FIG. 2. From the mixing tank (30), the first mixture is passed into the homogenizer (40), and is then recirculated through return piping (42) to the mixing tank (30). After this recirculation has been carried out for a sufficient time, as determined by the droplet size of the coarse emulsion, the coarse emulsion is all delivered to the mixing tank (30), from which it then passes through the microfluidizer (50) using an alternative discharge outlet. From the microfluidizer (50) the formed microemulsion may be passed further to processing, such as filtration, sterilization, and filling (60), or it may be recirculated back to the mixing tank (30) through return line (43).

One advantage of the apparatus as illustrated in FIG. 2 over that in FIG. 1 is that from the mixing tank (30) the first mixture can pass through the homogenizer (40) once, pass through the microfluidizer (50) once, and pass to the further processing step. In some embodiments only one pass through each of the homogenizer and microfluidizer is required. Such single pass preparation is appropriate for formulations where formation of a microemulsion having the desired droplet size can be achieved in a single pass.

The microfluidization conditions, including pressure and number of coarse emulsion passes through the microfluidizer, are dependent upon achieving the specified droplet size or droplet size distribution criteria. In some embodiments of the present invention, the coarse emulsion is passed through the microfluidizer, and, after each successive pass through the microfluidizer, a sample of the emulsion is collected and analyzed for droplet size and/or droplet size distribution. The number of passes required for a particular process may then be determined by the combination of temperature, pressure, and the number of times the coarse mixture is recirculated through the low pressure in-line homogenizer. In some embodiments the desired droplet size of the microemulsion is determined by meeting requirements for the D10, D50, and D90 droplet sizes set forth above.

Once a desired microemulsion is achieved, the microemulsion may be passed to the sterile filtration step prior to combining it with the bulk sterilized polymer system. The microemulsion of this invention is stable and can maintain its stability for 72 hours prior to use as discussed below.

The process of this invention can be applied to the preparation of polymer based emulsion systems. The final processing including product pH adjustment or neutralization of polymer pH is product specific and will depend upon the specific ingredients employed, the product application and applicable regulatory requirements.

Stability

The microemulsion of the present invention is stable for a sufficiently long period to either deliver the active pharmaceutical ingredient to a patient, or to allow the microemulsion to be stabilized further. The microemulsion may be stable for more than 5 years, or for more than 6 months, or for more than 30 days or for more than 72 hours.

In cases where the stability profile of the microemulsion does not meet the stability criteria set forth by a regulatory body or by marketing considerations, additional steps to stabilize the microemulsion may be employed. Such stabilizing steps may include, for example, mixing the microemulsion with a polymeric stabilizer. The polymeric stabilizer may be used to prevent the droplets of the microemulsion from agglomerating, thus acting as a protective colloid. Examples of suitable polymeric stabilizers include polyvinyl alcohols; polyvinyl acetals; polyvinylpyrrolidones; polysaccharides in water-soluble form, such as starches (amylose and amylopectin), modified starches, celluloses and their carboxymethyl, methyl, hydroxyethyl, and hydroxypropyl derivatives; proteins, such as casein or caseinate, soy protein, gelatin; lignosulfonates; synthetic polymers such as poly(meth)acrylic acid, copolymers of (meth)acrylates with carboxyl-functional comonomer units, poly(meth)acrylamide, polyvinylsulfonic acids, and water-soluble copolymers thereof; melamine-formaldehyde sulfonates, naphthalene-formaldehyde sulfonates, styrene-maleic acid copolymers and vinyl ether-maleic acid copolymers, polyurethane stabilizers, acrylic copolymers bearing sulfonate groups, such as those available commercially under the trade mark LUPASOL (BASF), such as LUPASOL PA 140 or LUPASOL VFR; copolymers of acrylamide and acrylic acid, copolymers of alkyl acrylates and N-vinylpyrrolidone, such as those available under the trade mark Luviskol (e.g., LUVISKOL K 15, K 30 or K 90 from BASF); sodium polycarboxylates (Polyscience Inc.) or sodium poly(styrene sulfonate) (Polyscience Inc.); vinyl and methyl vinyl ether-maleic anhydride copolymers (e.g., GANTREZ AN, from ISP), ethylene, isobutylene or styrene-maleic anhydride copolymers, and methyl vinyl ether-maleic acid copolymers (GANTREZ S, from ISP).

Other embodiments of the present disclosure will be apparent to those skilled in the art from consideration of the specification and practice of the embodiments disclosed herein. It is intended that the specification and examples be considered as exemplary only, with a true scope of the disclosure being indicated by the following claims.

All documents mentioned herein are hereby incorporated by reference in their entirety or alternatively to provide the disclosure for which they were specifically relied upon, if applicable.

The foregoing embodiments are susceptible to considerable variation in practice. Accordingly, the embodiments are not intended to be limited to the specific examples set forth herein. Rather, the foregoing embodiments are within the spirit and scope of the following claims, including the equivalents thereof available as a matter of law.

The applicant(s) do not intend to dedicate any disclosed embodiments to the public, and to the extent any disclosed modifications or alterations may not literally fall within the scope of the claims, they are considered to be part hereof under the doctrine of equivalents.

The invention claimed is:

1. A method of preparing a stable oil-in-water microemulsion, comprising the steps of:
   (a) mixing an aqueous phase comprising a non-ionic surfactant, a polyol, and water to solubilize the surfactant and polyol in the aqueous phase, wherein the weight ratio of the surfactant to polyol to water is between 10:20:70 and 1:1:1, with an oil phase comprising a substantially water insoluble active pharmaceutical ingredient and a long-chain triglyceride to generate a mixture, wherein the weight ratio of the oil phase to the aqueous phase is between about 0.01:1 and 1:1;
   (b) passing the mixture produced in step (a) at least once through a homogenizer at a temperature of from about 20° C. to about 50° C. to generate a coarse emulsion; and
   (c) passing the coarse emulsion at least once through a microfluidizer at a pressure of from about 70 MPa to about 150 MPa to produce an oil-in-water microemulsion having a mean oil particle droplet size of between about 50 nm and 300 nm.

2. The method of claim 1, wherein the non-ionic surfactant is a polyoxyethylene derivative of a sorbitan ester.

3. The method of claim 1, wherein the non-ionic surfactant is polysorbate 80.

4. The method of claim 1, wherein the polyol is a sugar alcohol.

5. The method of claim 1, wherein the polyol is a glycerol.

6. The method of claim 1, wherein the weight ratio of the oil phase to the aqueous phase is from about 0.01:1 to about 0.1:1.

7. The method of claim 1, wherein the active pharmaceutical ingredient is selected from the group consisting of: paclitaxel, docetaxel, ortataxel taxane, and epothilone.

8. The method of claim 1, wherein the active pharmaceutical ingredient is selected from the group consisting of: geladanamycin, rapamycin, vancomycin, and bleomycin.

9. The method of claim 1, wherein the active pharmaceutical ingredient is selected from the group consisting of: thyroid hormone and melatonin.

10. The method of claim 1, wherein the active pharmaceutical ingredient is selected from the group consisting of: cyclosporine, tacrolimus, and mycophenolic acid.

11. The method of claim 1, wherein the active pharmaceutical ingredient is selected from the group consisting of: amiodarone, corticosteroid, propofol.

12. The method of claim 1, wherein the active pharmaceutical ingredient is selected from radiocontrast agents.

13. The method of claim 1, wherein the active pharmaceutical ingredient is selected from the group consisting of: camptothecin, colchicine, amphotericin, cyclosporine, mycophenolic acid, ifosfamide, vinorelbine, gemcitabine and thiotepa.

14. The method of claim 1, wherein the active pharmaceutical ingredient is cyclosporine.

15. The method of claim 1, further comprising the step of
(d) filtering the microemulsion through a 0.2 µm filter.

16. The method of claim 15, further comprising the step of
(e) mixing the microemulsion with a polymeric stabilizer after the filtration step (d).

17. The method of claim 16, wherein the polymeric stabilizer is selected from the group consisting of: polyvinyl alcohol, polyvinyl acetal, polyvinylpyrrolidone, and polysaccharide.

18. An oil-in-water emulsion for delivering a substantially water insoluble active pharmaceutical ingredient produced by the method of claim 1.

19. The method of claim 1, wherein the pressure in step (c) is from about 125 MPa to about 150 MPa.

* * * * *